US010745540B2

(12) United States Patent
Borowski et al.

(10) Patent No.: US 10,745,540 B2
(45) Date of Patent: Aug. 18, 2020

(54) PROTECTION AND SELECTIVE RELEASE OF COLORANT

(71) Applicant: CAREFUSION 2200, INC., San Diego, CA (US)

(72) Inventors: Brandon Borowski, Winthrop Harbor, IL (US); Nathan Sieracki, Deerfield, IL (US)

(73) Assignee: CAREFUSION 2200, INC., San Diego, CA (US)

( * ) Notice: Subject to any disclaimer, the term of this patent is extended or adjusted under 35 U.S.C. 154(b) by 148 days.

(21) Appl. No.: 15/666,414

(22) Filed: Aug. 1, 2017

(65) Prior Publication Data

US 2019/0040232 A1 Feb. 7, 2019

(51) Int. Cl.
| | |
|---|---|
| *C08K 5/42* | (2006.01) |
| *A01N 25/10* | (2006.01) |
| *A01N 37/36* | (2006.01) |
| *A61L 2/18* | (2006.01) |
| *A61L 2/28* | (2006.01) |
| *A01N 25/00* | (2006.01) |

(52) U.S. Cl.
CPC ............... *C08K 5/42* (2013.01); *A01N 25/00* (2013.01); *A01N 25/10* (2013.01); *A01N 37/36* (2013.01); *A61L 2/18* (2013.01); *A61L 2/28* (2013.01)

(58) Field of Classification Search
CPC .......... C08K 5/42; A01N 25/00; A01N 37/36; A01N 25/10; A01N 31/02; A01N 47/44; A61L 2/28; A61L 2/18; C09B 67/0097; C09B 67/0001
See application file for complete search history.

(56) References Cited

U.S. PATENT DOCUMENTS

| | | | | |
|---|---|---|---|---|
| 2,791,533 | A * | 5/1957 | Segal ................. | G01N 33/84 436/163 |
| 4,093,745 | A * | 6/1978 | Wood ................. | A61K 8/0241 424/69 |
| 4,788,055 | A * | 11/1988 | Fischer ................. | A61K 31/485 424/483 |
| 5,110,479 | A * | 5/1992 | Frommer ................. | B01J 47/14 210/282 |
| 6,040,269 | A | 3/2000 | Imoto et al. | |
| 6,151,123 | A | 11/2000 | Nielsen | |
| 6,399,081 | B1 * | 6/2002 | Nakanishi ................. | A61K 8/895 424/401 |

(Continued)

OTHER PUBLICATIONS

Dowex MSA-2 Ion Exchange Resin (11 pages) (available online 2015 and 2017) (Year: 2015).*
Amberlyst A21 2 pages (Year: 2011).*

*Primary Examiner* — Pamela H Weiss
(74) *Attorney, Agent, or Firm* — Arent Fox LLP

(57) ABSTRACT

Selectively-releasable colorant compositions that allow a controllable release of colorant molecules from resin in response to one or more specific environmental stimuli. The selectively-releasable colorant composition may comprise resin particles having colorant molecules reversibly bound thereto. The compositions of the present disclosure may also provide precise and uniform control of free colorant content in an environment and/or protection of the immobilized (i.e., unreleased) colorant from compromising environmental chemistries. The present disclosure also relates to methods of preparing and methods of using the compositions described herein.

19 Claims, 6 Drawing Sheets

Duolite™ AP143/1083 Resin

FD&C Yellow #6 (Y6)

Y6-Loaded Duolite™ Colorant-Resinate Complex (56) References Cited

U.S. PATENT DOCUMENTS

| | | | |
|---|---|---|---|
| 6,527,849 B2 | 3/2003 | Dry | |
| 9,085,192 B2* | 7/2015 | Clayton | B41M 5/165 |
| 2003/0078242 A1* | 4/2003 | Raad | A01N 31/12 |
| | | | 514/150 |
| 2004/0134010 A1* | 7/2004 | Tseng | A46B 11/00 |
| | | | 15/167.1 |
| 2008/0299220 A1* | 12/2008 | Tamarkin | A61K 9/0014 |
| | | | 424/600 |
| 2010/0209371 A1* | 8/2010 | Casado-Chaudanson | |
| | | | A61K 8/49 |
| | | | 424/63 |
| 2011/0209294 A1 | 9/2011 | Choi | |
| 2014/0212654 A1* | 7/2014 | Clayton | B41M 5/165 |
| | | | 428/323 |
| 2015/0057940 A1* | 2/2015 | Baym | G16C 20/30 |
| | | | 702/19 |
| 2016/0002480 A1 | 1/2016 | Van Hameren et al. | |
| 2016/0041486 A1 | 2/2016 | Hara et al. | |
| 2016/0287741 A1* | 10/2016 | Harris | A61K 33/38 |

\* cited by examiner

Figure 1

| Material | FTIR Bands (cm$^{-1}$) |
|---|---|
| Y6-Duolite™ Colorant-Resinate Complex | 3414.5, 3027.7 2919.3, 3027.7, 2919.3, 2100.5, 1616.8, 1548.4, 1474.9, 1420.1, 1380.6, 1180.8, 1114.5, 1027.8, 983.1, 888.2, 828.4, 743.8, 704.2, 666.8 |
| Duolite™ Resin | 3359.3, 3020.5, 2921.1, 1612.4, 1475.7, 1420.4, 1381.0, 1220.6, 1125.8, 975.3, 924.3, 888.5, 857.9, 825.6, 706.0 |
| FD&C Yellow 6 | 1618.4, 1550.2, 1499.5, 1388.9, 1176.6, 1116.8, 1030.9, 983.7, 898.0, 831.0, 745.6, 707.6, 669.3 |

PROTECTION AND SELECTIVE RELEASE OF COLORANT

BACKGROUND

Colorants have a wide variety of uses in various applications, including, for example, the coloring of certain antiseptic solutions. In such applications, it is often necessary to provide a precise and uniform colorant content in the colored product (for example, by reducing precipitation of colorant and/or release variability thereof). It is also often necessary to protect colorant from degradation (for example, when subjecting a product to sterilization procedures). In addition, it is also sometimes necessary to detect counterfeit products, confirm API quality and/or potency, confirm sterility, detect thermal stress, and/or detect impurities in such products. There is thus a need in the art for efficient and effective means for obtaining these effects.

SUMMARY

The present disclosure relates generally to selectively-releasable colorant compositions that allow a controllable release of colorant molecules from a resin in response to one or more environmental stimuli. The selectively-releasable colorant compositions of the present disclosure are designed to release colorant from resin in specific environments. The compositions of the present disclosure also provide control of free colorant content in an environment and/or protection of the immobilized (i.e., unreleased) colorant from compromising environmental chemistries. The present disclosure also relates generally to methods of making and methods of using the compositions described herein.

DETAILED DESCRIPTION OF THE INVENTION

The present disclosure relates generally to selectively-releasable colorant compositions that allow a controllable release of colorant molecules from a resin in response to one or more specific environmental stimuli. The selectively-releasable colorant compositions of the present disclosure release colorant from resin in certain environments. The compositions of the present disclosure may also provide precise and uniform control of free colorant content in an environment and/or protection of the immobilized (i.e., unreleased) colorant from compromising environmental chemistries. The present disclosure also relates generally to methods of preparing and methods of using the compositions described herein.

The selectively-releasable colorant composition may comprise resin particles having colorant molecules reversibly bound thereto, interchangeably referred to herein as a "colorant-resinate complex."

As used herein, the term "colorant" refers to any suitable substance used for coloring a material, including dyes, tints, and pigments. According to some aspects, the colorant is suitable for use with antiseptic solutions containing one or more antiseptic agents, including (but not limited to) biguanides (e.g., chlorhexidine salts). For example, according to some aspects, the antiseptic agent may be selected from the group consisting of chlorhexidine gluconate, chlorhexidine acetate, chlorhexidine, chlorhexidine hydrochloride, and any combination thereof. Examples of biguanides/biguanide derivatives other than chlorhexidine/chlorhexidine salts include but are not limited to alexidine, alexidine salts, polyhexamide, polyhexamide salts, polyaminopropyl biguanide, polyaminopropyl biguanide salts, and other alkyl biguanides. As used herein, the term "derivative" refers to a) a chemical substance that is related structurally to a first chemical substance and derivable from it; b) a compound that is formed from a similar first compound or a compound that can be imagined to arise from another first compound, if one atom of the first compound is replaced with another atom or group of atoms; c) a compound derived or obtained from a parent compound and containing essential elements of the parent compound; or d) a chemical compound that may be produced from an initial compound of similar structure in one or more steps. For example, the colorant may be suitable for use with a solution containing about 2% w/v chlorhexidine gluconate (CHG) in about 70% v/v isopropyl alcohol (IPA), such as that used in ChloraPrep™ applicators and/or other similar antiseptic applicators. Example descriptions of such applicators may be found, for example, in Applicant's copending U.S. application Ser. Nos. 14/046,582; 14/529,753; 14/566,608; 14/595,084; and Ser. No. 15/163,500; and U.S. Pat. Nos. 5,690,958; 6,536,975; 8,708,983; 8,899,859; 9,119,946; and 9,572,967, the disclosures of which are incorporated herein by reference in their entirety.

Examples of colorants useful according to the present disclosure include, but are not limited to, anionic dyes suitable for medical use, such as dyes approved by the Food and Drug Administration for use in food, and/or drugs and cosmetics (i.e., "D&C" or "FD&C" dyes). For example, the colorant may be selected from the group consisting of, but are not limited to, FD&C Blue No. 1 (Brilliant Blue FCF), FD&C Blue No. 2 (Indigo Carmine), FD&C Green No. 3 (Fast Green FCF), FD&C Red No. 3 (Erythrosine), FD&C Red No. 40 (Allura Red), FD&C Yellow No. 5 (Tartrazine), FD&C Yellow No. 6 (Sunset Yellow FCF), D&C Yellow No. 8 (Disodium Fluorescein), D&C Orange No. 4, and combinations thereof. Combinations may be implemented to arrive at a particular color. For example, an orange colorant may comprise both FD&C Red No. 40 and D&C Yellow No. 8.

As used herein the term "resin" refers to any material that is capable of binding (i.e., immobilizing) colorant molecules. The resin according to the present disclosure may also be suitable for use with antiseptic solutions as disclosed herein. According to some aspects, the resin may comprise one or more insoluble base polymeric units having monomers capable of forming reversible non-covalent interactions. According to some aspects, the resin is comprised of one or more insoluble particles.

For example, the resin may comprise an ion-exchange resin, e.g., an anion-exchange resin. According to some aspects, the ion-exchange resin may comprise one or more ion-exchange polymers. Examples of suitable ion-exchange resins include, but are not limited to a macroporous polymer matrix with quaternary amine functional group(s) (e.g., Duolite™ AP143-1083 or ScavengePore® phenethyl diethylamine), or a macroporous copolymer matrix with tertiary amine functional group(s) (e.g. Dowex® 66, AMBERLITE™ IRA96, or Amberlyst® A21).

According to some aspects, the resin may comprise an ion-exchange resin that has been pretreated to generate a complementary ionic partner to the intended colorant cargo, or to facilitate ion pairing with the intended colorant cargo. Examples of pretreatment agents useful for the preparation of resin according to the present disclosure include, but are not limited to, solutions containing one or more acids (e.g., hydrochloric acid), bases (e.g., sodium hydroxide), or salts (e.g., sodium chloride, sodium gluconate).

As used herein the term "resinate" refers to a resin material that has been loaded with the terminal cargo (e.g. colorant) required for the intended final application.

The colorant-resinate complex may comprise resin particles having colorant molecules reversibly bound thereto. As used herein, the term "reversibly bound" or "reversible binding" refers to an association between colorant molecules and resin such that a certain amount of colorant remains bound to the resin until the association is interrupted by certain environmental stimuli. For example, according to some aspects, at least 10% of the colorant molecules may remain bound to the resin until the association is interrupted by certain environmental stimuli, optionally at least 15%, optionally at least 20%, optionally at least 25%, optionally at least 30%, optionally at least 35%, optionally at least 40%, optionally at least 50%, optionally at least 60%, optionally at least 70%, optionally at least 80%, optionally at least 90%, optionally at least 95%, and optionally 100%. According to some aspects, colorant molecules bound to the resin and colorant molecules not bound to the resin in an environment may remain at a certain equilibrium, such that a certain amount of colorant molecules remain bound to the resin at all times until the association is interrupted. According to some aspects, the association between the colorant molecules and the resin may comprise one or more non-covalent interactions, including ionic interactions, hydrogen bonds, halogen bonds, Van de Waals forces, dipole-dipole interactions, dipole-induced dipole interactions, London dispersion forces, $\pi$-$\pi$ interactions, cation-$\pi$ interactions, hydrophobic interactions, and combinations thereof.

The association (e.g., the non-covalent interaction) between colorant molecules and resin may be interrupted, or "broken," by one or more environmental stimuli, interchangeably referred to herein as a "disassociation." It should be understood that disassociation between colorant molecules and resin may comprise a release of substantially all colorant molecules from the resin or, alternatively, releasing only a portion of the colorant molecules from the resin. Additionally, disassociation between colorant molecules and resin may comprise shifting the equilibrium between colorant molecules bound to the resin and colorant molecules not bound to the resin. For example, according to some aspects, at least 10% of the bound colorant molecules may be released from the resin when the association is interrupted by certain environmental stimuli (and/or a corresponding shift in equilibrium may be observed), optionally at least 15%, optionally at least 20%, optionally at least 25%, optionally at least 30%, optionally at least 35%, optionally at least 40%, optionally at least 50%, optionally at least 60%, optionally at least 70%, optionally at least 80%, optionally at least 90%, optionally at least 95%, and optionally 100%.

According to some aspects, the association between colorant molecules and resin in the colorant-resinate complex may be selected based on the responsiveness of the association to certain environmental stimuli. As used herein, the term "environment" refers to the immediate (i.e., in physical contact) surroundings of the colorant-resinate complex (e.g., an antiseptic solution). Examples of environmental stimuli that may interrupt colorant-resinate complex associations include, but are not limited to: the molecular weight of one or more components of the environment, the temperature of the environment, the pH of the environment, the pKa of one or more ionizable groups in the environment, the hydrophobicity of one or more components of the environment, the ionic strength of one or more components of the environment, and combinations thereof.

The responsiveness of the colorant-resinate complex associations to various environmental stimuli may be a result of one or more factors, including the type of associate (e.g., the type of one or more non-covalent interactions), the nature of the colorant molecules (e.g., composition, molecular weight, hydrophobicity, etc.), the nature of the resin (e.g., composition, molecular weight, hydrophobicity, etc.), the pretreatment agent used for preparing the resin, and combinations thereof. For example, the association between the colorant molecules and resin may be tailored to be responsive to (i.e., to be interrupted by or to remain uninterrupted by) a specific environmental stimulus or a combination of environmental stimuli. According to some aspects, the association between the colorant molecules and resin may also be tailored in order to control the degree of disassociation (e.g., the amount of colorant released from the resin and/or the shift in equilibrium between colorant molecules bound to the resin and colorant molecules not bound to the resin) in response to a certain environmental stimulus or a combination of environmental stimuli.

For example, the association between colorant molecules and resin may be selected to include more than one type of non-covalent interaction. In this way, the release of colorant molecules from resin may be tailored, for example, such that molecules are released only if a certain combination of environmental stimuli is present. In another example, an association comprising more than one type of non-covalent interaction may provide a variable shift in equilibrium between colorant molecules bound to the resin and colorant molecules not bound to the resin based on the cumulative combination of certain stimuli present in an environment. According to some aspects, the association between colorant molecules and resin may include one, two, three, four, five, or more types of non-covalent interactions.

According to some aspects, all of the colorant molecules present in the colorant-resinate complex may be bound to the resin via the same type of association. Alternatively, one or more portions of the colorant molecules present in the colorant-resinate complex may be bound to the resin via a different association than another portion. In this way, each portion of a colorant molecule may dissociate in response to unique environmental conditions. Alternatively or additionally, certain colorant molecules may be released to a greater extent than other colorant molecules in response to certain environmental stimuli.

According to some aspects, one or more associations of the colorant-resinate complex may be influenced or affected by other associations present in the colorant-resinate complex. For example, one or more associations may be strengthened or weakened by the presence of one or more other association(s) and/or the interruption of one or more other association(s). In one example, a colorant molecule may be bound to resin via at least a first association and a second association of equivalent strengths. In this example, the first association may be strengthened or weakened by the interruption of the second association, thereby altering the extent that the colorant molecule bound by the first and second association disassociates from the resin. It should be understood that in this example, the at least first and second association may be the same or different. It should also be understood that the first association may alternatively or additionally be affected by an association other than the second association (e.g., a third association between the colorant molecule and resin and/or an association between a different colorant molecule and resin).

The present disclosure also relates to methods of making colorant-resinate complexes as described herein. The method may include providing an ion-exchange resin, optionally pretreating the ion-exchange resins with a pretreatment agent, and combining the resin with colorant molecules, thereby binding colorant molecules to (i.e., immobilizing colorant molecules on) the resin via one or more associations.

According to some aspects, the optional pretreatment step may comprise combining a suitable ion-exchange resin with a pretreatment agent for an amount of time sufficient for altering the surface properties of the ion-exchange resin. For example, the ion-exchange resin may be combined with a pretreatment agent such that the surface of the ion-exchange resin is functionalized with one or more functional groups. It should be understood that the pretreatment agent may be selected in order to provide a resin adequate for preparing a colorant-resinate complex having a desired environmentally-sensitive association between colorant molecules and resin. For example, the optional pretreatment step may comprise combining a solution containing ion-exchange resin particles with a pretreatment agent for a certain period of time, washing the combined solution, filtering the combined solution, and drying the resulting resin particles.

The method may also comprised binding colorant molecules to the resin by combining the colorant molecules with the resin for an amount of time sufficient for immobilizing the colorant molecules on the resin via one or more specific associations. For example, the binding step may comprise combining a solution containing resin particles with a solution containing colorant molecules for a certain period of time, washing the combined solution, filtering the combined solution, and drying the resulting colorant-resinate complexes.

According to some aspects, the selectively-releasable colorant composition may be provided with an applicator, for example, an applicator designed for applying one or more antiseptic solutions. For example, the applicator may comprise a body having one or more ampoules and/or similar containers in which an antiseptic solution may be contained prior to application. Suitable applicators may be found, for example, in Applicant's copending U.S. application Ser. Nos. 14/046,582; 14/529,753; 14/566,608; 14/595,084; and 15/163,500; and U.S. Pat. Nos. 5,690,958; 6,536,975; 8,708,983; 8,899,859; 9,119,946; and 9,572,967, the disclosures of which are incorporated herein by reference in their entirety. According to some aspects, the selectively-releasable colorant composition may be provided with the one or more ampoules and/or similar containers, for example, on one or more internal walls thereof. The selectively-releasable colorant composition may therefore contact the antiseptic solution for any of the uses described herein. Additionally or alternatively, the selectively-releasable colorant composition may be provided with any portion of the applicator and contact is established with the antiseptic solution upon activation of the device and prior to application.

For example, according to some aspects, the applicator may comprise one or more fluid metering devices, such as a sponge, plug, or pledget, or other porous material. For example, the fluid metering device may be positioned between an application member of the applicator and one or more ampoules and/or similar containers for containing the antiseptic solution. The fluid metering device may, for example, be configured to control the rate the antiseptic solution flows from the one or more ampoules and/or similar containers to the application member, provide dye to the antiseptic solution, and/or prevent shards of glass from pushing through the application member during use of the applicator. According to some aspects, the fluid metering device may be provided with the selectively-releasable colorant composition (e.g., via impregnation) such that the selectively-releasable colorant composition contacts the antiseptic solution as the antiseptic solution flows through the fluid metering device.

The present disclosure also relates to methods of using colorant-resinate complexes as described herein. According to some aspects, the method may comprise combining one or more colorant-resinate complexes with a desired product. For example, colorant-resinate complexes may be combined with drug product units to provide precise and uniform control of the free colorant content therein. Additionally or alternatively, the colorant-resinate complexes may be combined with drug product units to stabilize colorant molecules from environmental chemistries. For example, colorant-resinate complexes may be combined with drug product units prior to sterilization to protect the colorant from chemistries associated with sterilization (e.g., chemistries associated with sterilization using heat, steam, ethylene oxide, peroxide, and/or peracetic acid), wherein the colorant would degrade or be otherwise compromised by the sterilization process if it was not part of the colorant-resinate complex. In another example, the colorant-resinate complexes may be combined with drug product units to protect the colorant from chemistries that may affect shelf life (e.g., thermal and/or light stress, such as from UV and/or visible light), wherein the colorant would degrade or be otherwise compromised by such chemistries if it was not part of the colorant-resinate complex.

For example, according to some aspects, at least 50% of the colorant may remain uncompromised after sterilization and/or after a certain period of shelf life, optionally at least 55%, optionally at least 60%, optionally at least 65%, optionally at least 70%, optionally at least 75%, optionally at least 80%, optionally at least 85%, optionally at least 90%, optionally at least 95%, and optionally at least 100%. The term "shelf life" refers to the length of time that a product may be stored without becoming unfit for its intended purpose and/or unable to demonstrate regulatory compliance. According to some aspects, the period of shelf life may be at least 1 month, optionally at least 2 months, optionally at least 3 months, optionally at least 4 months, optionally at least 5 months, optionally at least 6 months, optionally at least 7 months, optionally at least 8 months, optionally at least 9 months, optionally at least 10 months, optionally at least 11 months, optionally at least 12 months, optionally at least 24 months, and optionally at least 36 months. As used herein, the term "uncompromised" refers to a component's ability to function adequately for a specified purpose (e.g., a colorant's ability to adequately color a solution and/or demonstrate regulatory compliance).

The colorant-resinate complexes may also reduce or eliminate precipitation of colorant molecules and/or release variability thereof.

In another example, the colorant-resinate complexes may be combined with a drug solution to determine the identity and/or quality thereof. For example, the method may include combining one or more colorant-resinate complexes with a product and observing the product for color change, wherein color change indicates the presence or absence of one or more certain environmental stimuli. Similarly, the colorant-resinate complexes may be combined with a drug solution to provide visual information on the binary presence or absence of one or more particular ingredients, with applications in counterfeit detection. Example uses of the colorant-resinate complexes according to the present disclosure also include, but are not limited to, visual confirmation of active pharmaceutical ingredient (API) quality/potency, visual confirmation of sterility, thermal stress indication, specified or total impurity detection, and combinations thereof.

While the aspects described herein have been described in conjunction with the example aspects outlined above, various alternatives, modifications, variations, improvements, and/or substantial equivalents, whether known or that are or may be presently unforeseen, may become apparent to those having at least ordinary skill in the art. Accordingly, the example aspects, as set forth above, are intended to be illustrative, not limiting. Various changes may be made without departing from the spirit and scope of the disclosure. Therefore, the disclosure is intended to embrace all known or later-developed alternatives, modifications, variations, improvements, and/or substantial equivalents.

Thus, the claims are not intended to be limited to the aspects shown herein, but are to be accorded the full scope consistent with the language of the claims, wherein reference to an element in the singular is not intended to mean "one and only one" unless specifically so stated, but rather "one or more." All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed as a means plus function unless the element is expressly recited using the phrase "means for."

Further, the word "example" is used herein to mean "serving as an example, instance, or illustration." Any aspect described herein as "example" is not necessarily to be construed as preferred or advantageous over other aspects. Unless specifically stated otherwise, the term "some" refers to one or more. Combinations such as "at least one of A, B, or C," "at least one of A, B, and C," and "A, B, C, or any combination thereof" include any combination of A, B, and/or C, and may include multiples of A, multiples of B, or multiples of C. Specifically, combinations such as "at least one of A, B, or C," "at least one of A, B, and C," and "A, B, C, or any combination thereof" may be A only, B only, C only, A and B, A and C, B and C, or A and B and C, where any such combinations may contain one or more member or members of A, B, or C. Nothing disclosed herein is intended to be dedicated to the public regardless of whether such disclosure is explicitly recited in the claims.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, dimensions, etc.) but some experimental errors and deviations should be accounted for.

EXAMPLES

Example 1

Preparation of a Yellow 6-Loaded Duolite™ AP143-1083 Colorant-Resinate Complex

Experiments were performed at room temperature under normal indoor lighting conditions. FTIR spectra were collected directly from solid powders using an Agilent Cary 630 FTIR spectrophotometer fitted with a diamond ATR attachment. Spectra were collected from 4000-500 $cm^{-1}$ at a resolution of 4 $cm^{-1}$.

Figure 1:
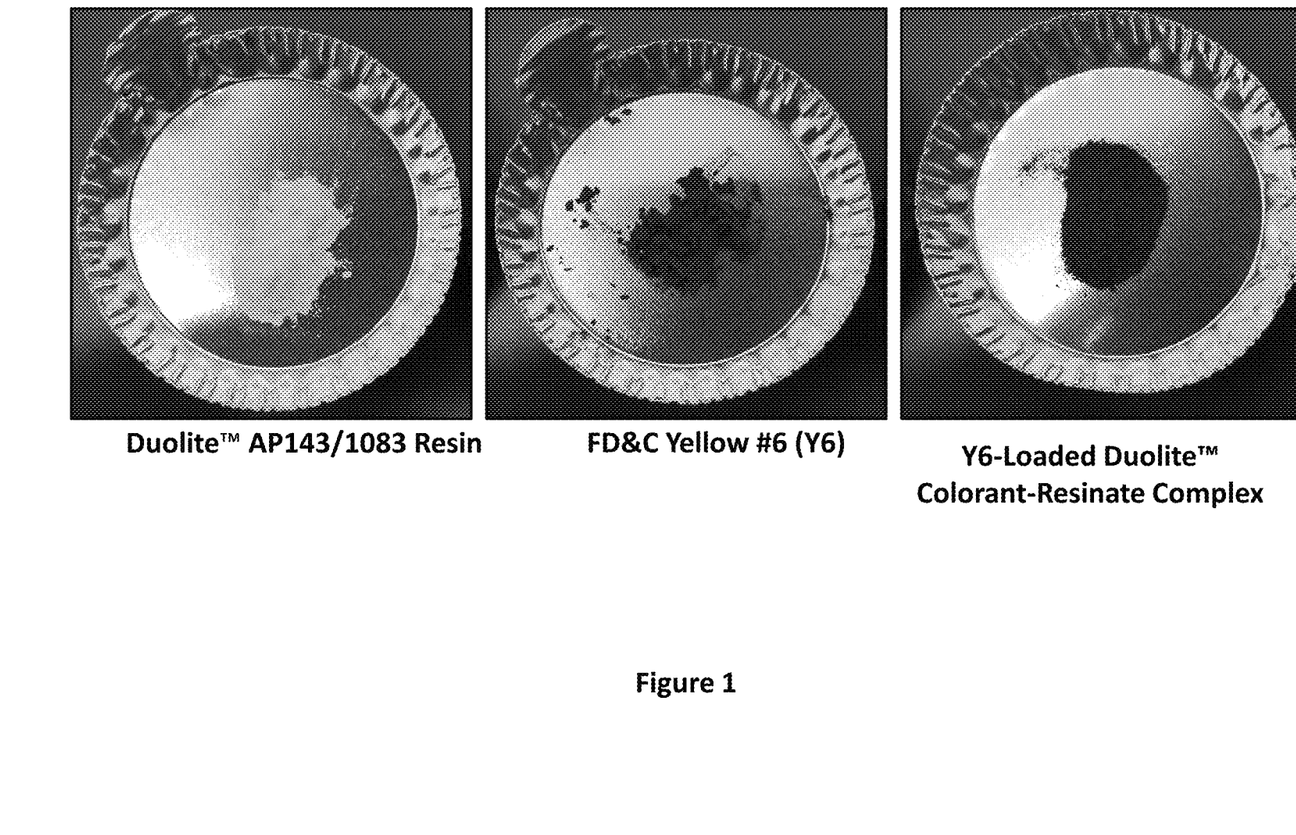
FIG. 1 shows photographs of the colorant-resinate complex prepared according to Example 1 in comparison to the unloaded resin matrix and the free colorant compound.
Figure 2:
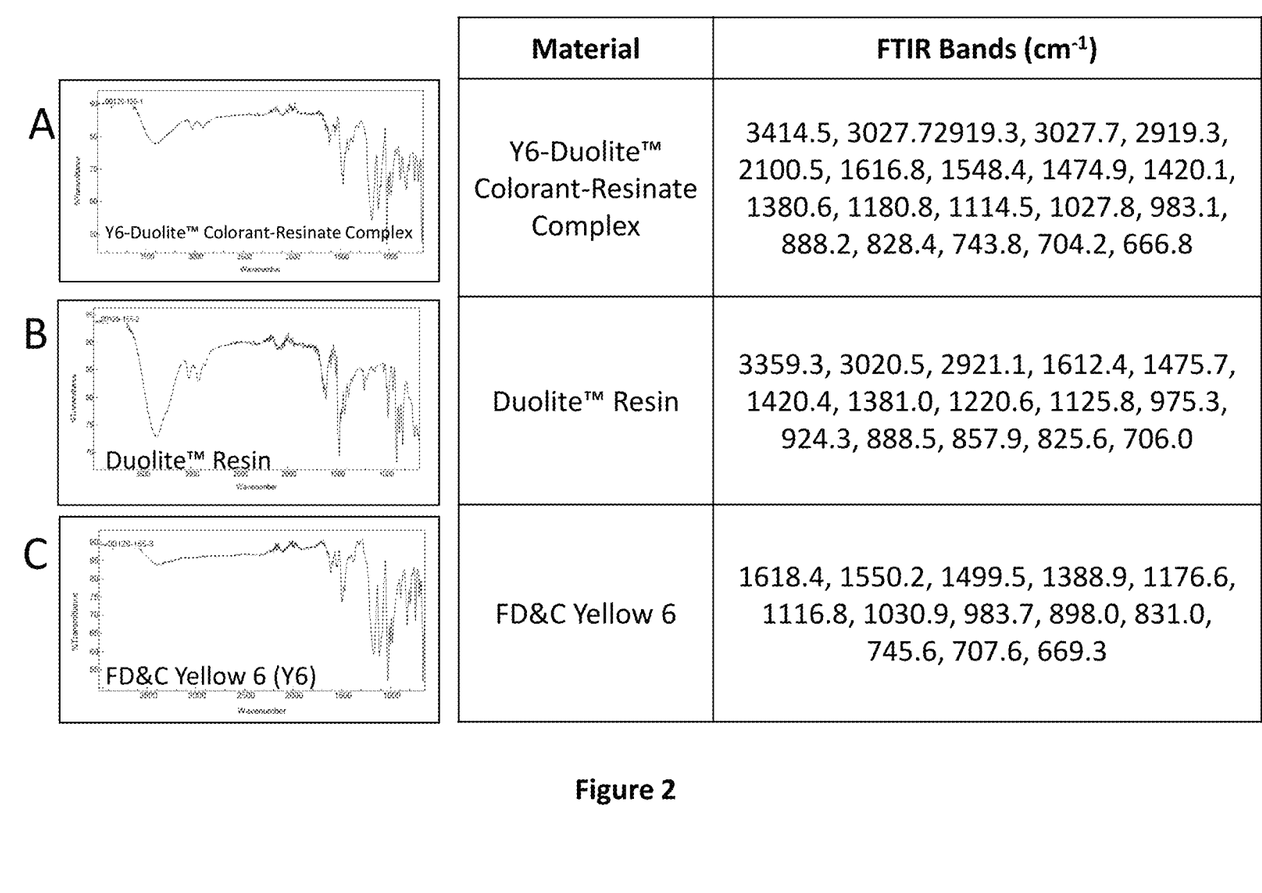
FIG. 2 shows FTIR spectra for the colorant-resinate complex prepared according to Example 1 in comparison to the unloaded resin matrix and the free colorant compound.

To a 1 L Erlenmeyer flask, 250 mL purified water and 3.00 g Duolite™ AP143/1083 anion exchange resin (Dow Chemical Company) was added. The flask was stirred at a setting of 200 rpm allowing the resin to completely disperse. To a 300 mL glass beaker, 250 mL purified water and 2.987 g FD&C Yellow No. 6 (Y6) (Sensient Colors, Inc.) was added. The mixture was stirred until completely dissolved, loaded into an addition funnel, and added drop wise to the stirring solution of Duolite™ resin over the course of 30 minutes. After addition was complete, the resulting mixture was allowed to stir for an additional 30 minutes. The stir bar was removed, and the colorant-resinate complex was allowed to settle. The supernatant was decanted, and the colorant-resinate complex was diluted with 900 mL of purified water with stirring. The solution was again allowed to settle, and the process was repeated for a total of three washes (3×900 mL). The dark red colorant-resinate complex was collected via vacuum filtration, and the resulting cake was washed with purified water (6×100 mL) and dried overnight at 40° C. to yield 2.94 g Yellow No. 6-loaded resinate as a dark red solid (FIG. 1). The product was characterized by FTIR spectroscopy (FIG. 2).

Example 2

Using a Colorant-Resinate Complex to Selectively Color Drug Solution

The selective release of colorant from the colorant-resinate complex obtained in Example 1 was evaluated following exposure to each of the following solutions.
- Sample 1: A solution containing Purified Water
- Sample 2: A solution containing 100% Isopropyl Alcohol
- Sample 3: A solution containing 70% v/v Isopropyl Alcohol
- Sample 4: An aqueous solution containing 2% w/v chlorhexidine gluconate Sample 5: A solution containing 2% w/v chlorhexidine gluconate in 70% v/v isopropyl alcohol (i.e., such as that used in ChloraPrep™ products)

Figure 3:
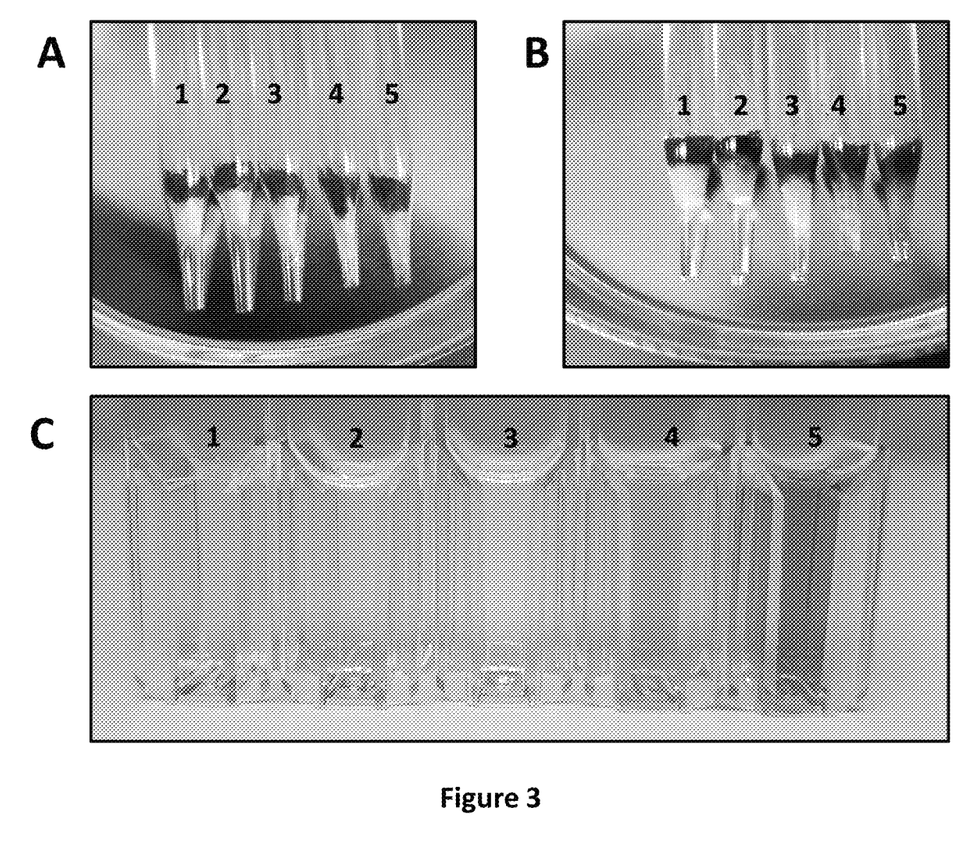
FIG. 3 shows the results of the selective release experiment described in Example 2.

To evaluate each solution, 20 mg of the colorant-resinate complex was loaded into each of five separate glass columns. To each column was added 1 mL of one of the five sample solutions, and the flow-through was collected and imaged. As shown in FIG. 3, the results showed that Sample 5 was colored to the greatest extent among all samples (i.e., contained the highest level of released colorant) while minimal dye was released with Solution 4, and no visibly detectable dye was released using Sample solutions 1, 2, or 3.

The requirement for both organic solvent and a salted environment for maximal release of colorant into solution suggests that the dye is bound to the resin through both hydrophobic (thereby weakened by increased organic phase) and ionic (thereby weakened by enhanced solution ionic strength) interactions, and that both interactions must be overcome for the dye to be efficiently released from the resin.

Figure 4:
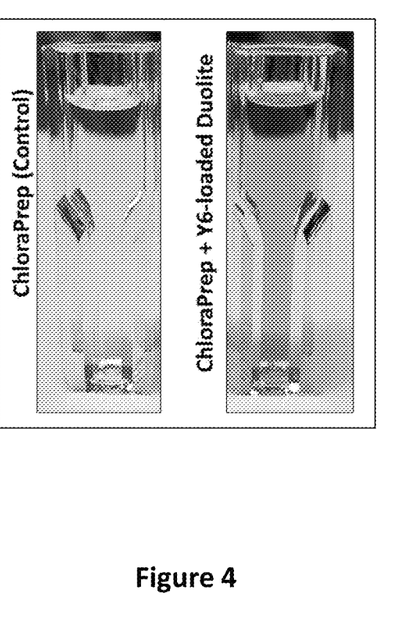
FIG. 4 shows a photographic comparison between untreated and Yellow 6-loaded Duolite™ colorant-resinate complex-treated ChloraPrep™ according to Example 2.

Evaluation of the critical chemical quality attributes of ChloraPrep™ solution (250 mL) was conducted before and after exposure to 50 mg of Y6-loaded Duolite™ AP143-1083 colorant-resinate with stirring for two hours to ensure maximum ion exchange. Shown in FIG. 4 is a photographic comparison of untreated and Y6-loaded Duolite™ colorant-resinate complex-treated ChloraPrep™, demonstrating the resulting orange tinted solution following exposure to the resinate.

As shown in Table 1 below, the critical chemical quality attributes of the ChloraPrep™ solution were not significantly influenced following treatment with the Y6-loaded Duolite™ colorant-resinate complex. Neither the CHG content nor the IPA content was significantly altered following treatment with the colorant-resinate complex. Importantly, assessment of gluconate content (the presumed species undergoing ion-exchange to release colorant from the resin) in the ChloraPrep™ solution revealed no significant change following treatment with the resin. Furthermore, neither the total related substances (TRS) content nor the p-chloroaniline (PCA) content (a specified and regulated impurity) were significantly influenced following two hours of treatment with Y6-loaded Duolite™ colorant-resinate complex. These results suggest that a negligible fraction of the total gluconate pool was required to color the solution, and that the coloring mechanism is chemically compatible with the ChloraPrep™ formulation.

TABLE 1

| Attribute | Control (untreated ChloraPrep ™) | Chloraprep ™ + Y6-loaded Duolite ™ Colorant-Resinate Complex |
| --- | --- | --- |
| Chlorhexidine Gluconate[1] (% w/v) | 1.97 | 1.97 |
| Gluconate[2] (mg/ml) | 8.37 | 8.36 |
| Isopropyl Alcohol (% v/v) | 69.8 | 69.5 |
| Total Related Rubstances (%) | 1.28 | 1.27 |
| p-Chloroaniline (ppm) | 5 | 5 |

[1]Calculated from determination chlorhexidine (base) content assuming no change in gluconate content
[2]Measured as titratable base equivalents Example 3

Protection of Colorant from Ethylene Oxide Using Colorant-Resinate Complex

Figure 5:
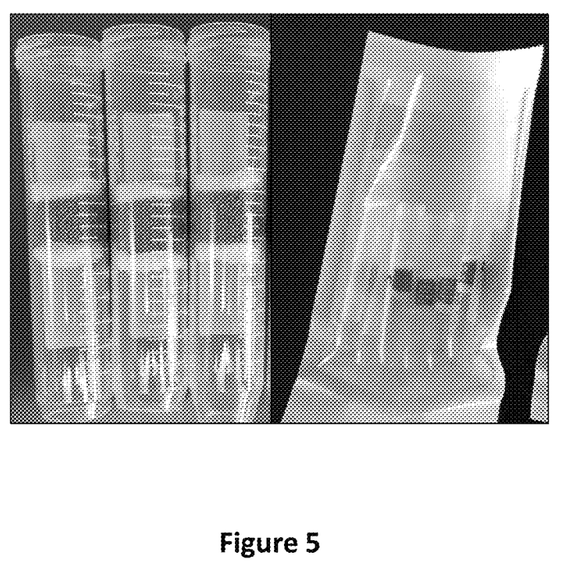
FIG. 5 shows a photograph of the colorant-resinate complex immobilized within a plastic centrifuge tube and capped by polyester novenette material according to Example 3.

First, a colorant-resinate complex comprising Dowex® 66 ion exchange resin (Dow Chemical Company) and D&C Yellow No. 8 (Y8) (Sensient Colors, Inc.) was prepared according to the method of the invention. As shown in FIG. 5, the colorant-resinate complex was then immobilized within a plastic centrifuge tube and capped by polyester novenette material to allow ethylene oxide (EtO) gas penetration.

Control pledgets were then prepared by dipping polyester pledgets into Y8 tinting solution and drying, or by atomizing spray loading of Max Tint (a combination of D&C Yellow 8 (Y8) and FD&C Red 40 (R40)) onto pledgets comprised of 50:50 polyethylene:polypropylene. Each of the control pledgets were immobilized into plastic syringes in an identical fashion to the colorant-resinate complex. Two (2) syringes of each material were loaded into each of three (3) plastic sterilization bags and sealed. One (1) sterilization bag would serve as a control (unsterilized) while the others bags would undergo either one cycle (1×EtO) or two cycles (2×EtO) of EtO treatment.

Following EtO treatment, Y8 was extracted from each sample and was quantified (relative to internal impurities) using HPLC. As shown in Table 2, all control (i.e., untreated by EtO gas) samples showed a single peak in the HPLC spectrum attributable to the fluorescein moiety. In each case, treatment with 1×EtO gas resulted in a decrease of fluorescein in the total extract, while a second treatment (2×EtO) resulted in a further decrease in contribution of fluorescein. Notably, the colorant-resinate complex showed greater relative protection of fluorescein after a single EtO treatment (79.6% fluorescein remaining compared to 53.4% or 61.8% for Y8 and Y8/R40 samples, respectively). The protective effect was more dramatic following a second treatment with EtO (65.4% fluorescein remaining compared to 21.2% or 24.1% for Y8 and Y8/R40 samples, respectively.

TABLE 2

| | Host Material | | |
| --- | --- | --- | --- |
| | Polyester Pledget | 50:50 PE:PP Pledget | Dowex ® 66 Resin |
| | Dye | | |
| Treatment | Yellow 8 | Yellow 8/Red 40 | Yellow 8 |
| | % Yellow Remaining | | |
| Control | 100.0 | 100.0 | 100.0 |
| 1xEtO | 53.4 | 61.8 | 79.6 |
| 2xEtO | 21.2 | 24.1 | 65.4 |

Figure 6:
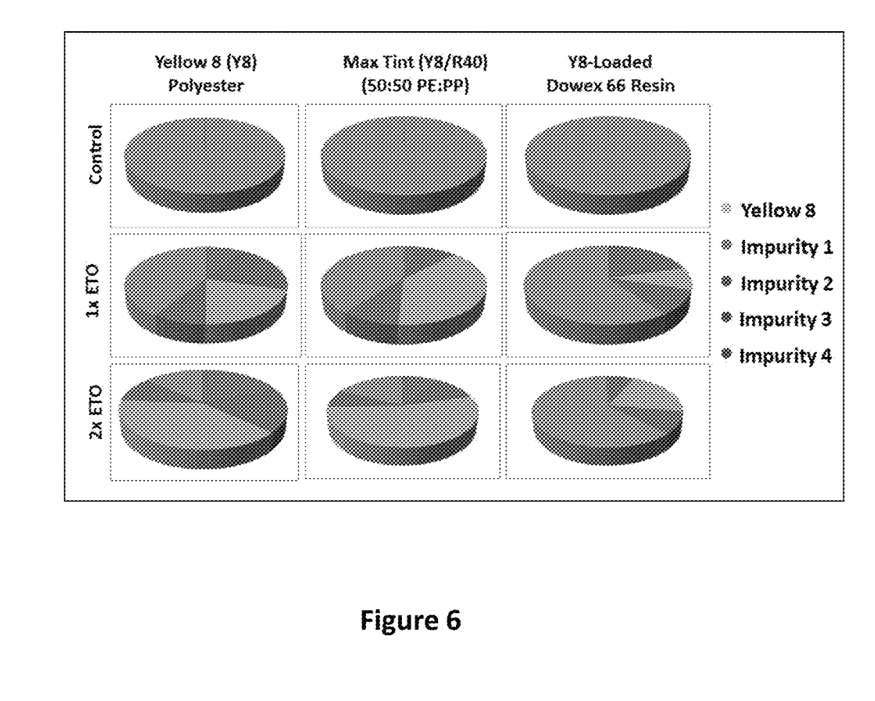
FIG. 6 shows the relative total area contribution from dye-related extract components identified by HPLC according to Example 3.

The relative total area contribution from extract components identified by HPLC (254 nm) are summarized in FIG. 6 for all samples tested. As can be seen by FIG. 6, it is clear that EtO gas treatment resulted in chemical modification of fluorescein in all cases, and that a second treatment resulted in further modification. Importantly, the colorant-resinate complex provided significant protection of immobilized fluorescein from chemical modification from the EtO gas through two full cycles.

The invention claimed is:
1. A solution comprising:
a selectively-releasable colorant composition comprising one or more resin particles having colorant molecules reversibly bound thereto via an association, about 2% w/v chlorhexidine or a salt thereof, and
about 70% v/v isopropyl alcohol.

2. The solution of claim 1, wherein the one or more resin particles comprises one or more ion-exchange polymers.

3. The solution of claim 2, wherein the one or more ion-exchange polymers has been functionalized by one or more pretreatment agents.

4. The solution of claim 1, wherein the colorant is a dye.

5. The solution of claim 1, wherein the colorant is selected from the group consisting of FD&C Blue No. 1 (Brilliant Blue FCF), FD&C Blue No. 2 (Indigo Carmine), FD&C Green No. 3 (Fast Green FCF), FD&C Red No. 3 (Erythrosine), FD&C Red No. 40 (Allura Red), FD&C Yellow No. 5 (Tartrazine), FD&C Yellow No. 6 (Sunset Yellow FCF), D&C Yellow No. 8 (Disodium Fluorescein), D&C Orange No. 4, and any combinations thereof.

6. The solution of claim 1, wherein the association comprises one or more non-covalent interactions.

7. The solution of claim 6, wherein the non-covalent interactions are selected from the group consisting of ionic interactions, hydrogen bonds, halogen bonds, Van de Waals forces, dipole-dipole interactions, dipole-induced dipole interactions, London dispersion forces, π-π interactions, cation-π interactions, hydrophobic interactions, and combination thereof.

8. The solution of claim 7, wherein the association comprises at least two different non-covalent interactions.

9. The solution of claim 1,
wherein at least a portion of the colorant molecules dissociates from the one or more resin particles in response to one or more environmental stimuli, and
wherein the one or more environmental stimuli is selected from the group consisting of a molecular weight of one or more components of the environment, a temperature of the environment, a pH of the environment, a pKa of one or more ionizable groups in the environment, a hydrophobicity of one or more components of the environment, an ionic strength of one or more components of the environment, and combinations thereof.

10. The solution of claim 9, wherein disassociation comprises a shift in an equilibrium between colorant molecules bound to the one or more resin particles and colorant molecules not bound to the one or more resin particles.

11. The solution of claim 9, wherein the one or more environmental stimuli comprises at least two stimuli.

12. A method of making the solution of claim 1 comprising:
providing the one or more resin particles,
combining the one or more resin particles with the colorant molecules, thereby binding the colorant molecules to the one or more resin particles via the association to provide the selectively-releasable colorant composition, and
combining the selectively-releasable colorant composition with the chlorhexidine or salt thereof and the isopropyl alcohol to provide the solution.

13. The method according to claim 12, wherein the one or more resin particles are prepared by combining ion-exchange resin particles with a pretreatment agent such that the ion-exchange resin particles are functionalized with one or more functional groups.

14. The method of claim 12, wherein the solution combined product is sterilized and/or stored for a period of shelf life, wherein at least 65% of the colorant molecules are uncompromised by the sterilization and/or the period of shelf life.

15. The method of claim 14, wherein the solution is sterilized using ethylene oxide.

16. An antiseptic applicator, wherein the applicator comprises:
one or more ampoules containing the solution of claim 1; and
an application member.

17. The solution of claim 1, wherein the chlorhexidine or salt thereof comprises at least chlorhexidine gluconate.

18. The solution of claim 1, wherein the chlorhexidine or salt thereof comprises at least chlorhexidine acetate.

19. The solution of claim 1, wherein the chlorhexidine or salt thereof comprises at least chlorhexidine dihydrochloride.

* * * * *